US00PP28562P2

(12) United States Plant Patent
Sato et al.

(10) Patent No.: US PP28,562 P2
(45) Date of Patent: Oct. 24, 2017

(54) **NEW GUINEA *IMPATIENS* PLANT NAMED 'SAKIMP038'**

(50) Latin Name: ***Impatiens×hybrida* hort**
Varietal Denomination: SAKIMP038

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,133

(22) Filed: Mar. 31, 2016

(51) Int. Cl.
*A01H 5/08* (2006.01)

(52) U.S. Cl.
USPC ..... Plt./318.3

(58) Field of Classification Search
USPC ..... Plt./318.3
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *Impatiens* plant particularly distinguished by having orange-red flowers, and green leaves with yellow variegation, is disclosed.

2 Drawing Sheets

Genus and species: *Impatiens×hybrida* hort.
Variety denomination: 'SAKIMP038'.

BACKGROUND OF THE NEW PLANT

The present invention comprises a new and distinct variety of New Guinea *impatiens* plant, botanically known as *Impatiens×hybrida* hort, and referred to by the variety name 'SAKIMP038'. 'SAKIMP038' originated from a hybridization between the proprietary female *Impatiens* line 'NG-02SM-13' (unpatented) and the proprietary male *Impatiens* line 'NF-457BB' (unpatented) in Misato, Japan.

In September 2009, the parental lines were crossed and a population of F1 plants was created. The F1 plants were evaluated in Misato, Japan in an open field trial. The criteria for selection included bright flower color, clear variegation, and a strong root system. At the completion of the trial, a single plant selection designated as 'M2011-377' was selected based on the above selection criteria an vegetatively propagated. From June to August 2011, the selection was evaluated in an open field in Misato, Japan. Shoot-tip cuttings of the variety were then shipped to Salinas, Calif., where the plants were regenerated and re-evaluated for stability of traits. 'M2011-377' was subsequently named 'SAKIMP038', which was found to reproduce true to type in successive generations of asexual propagation via vegetative shoot-tip cuttings in Salinas, Calif.

SUMMARY

The following are the most outstanding and distinguishing characteristics of this new variety when grown under normal horticultural practices in Salinas, Calif.

1. Orange-red flowers; and
2. Green leaves with yellow variegation.

DESCRIPTION OF THE PHOTOGRAPHS

This *Impatiens* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
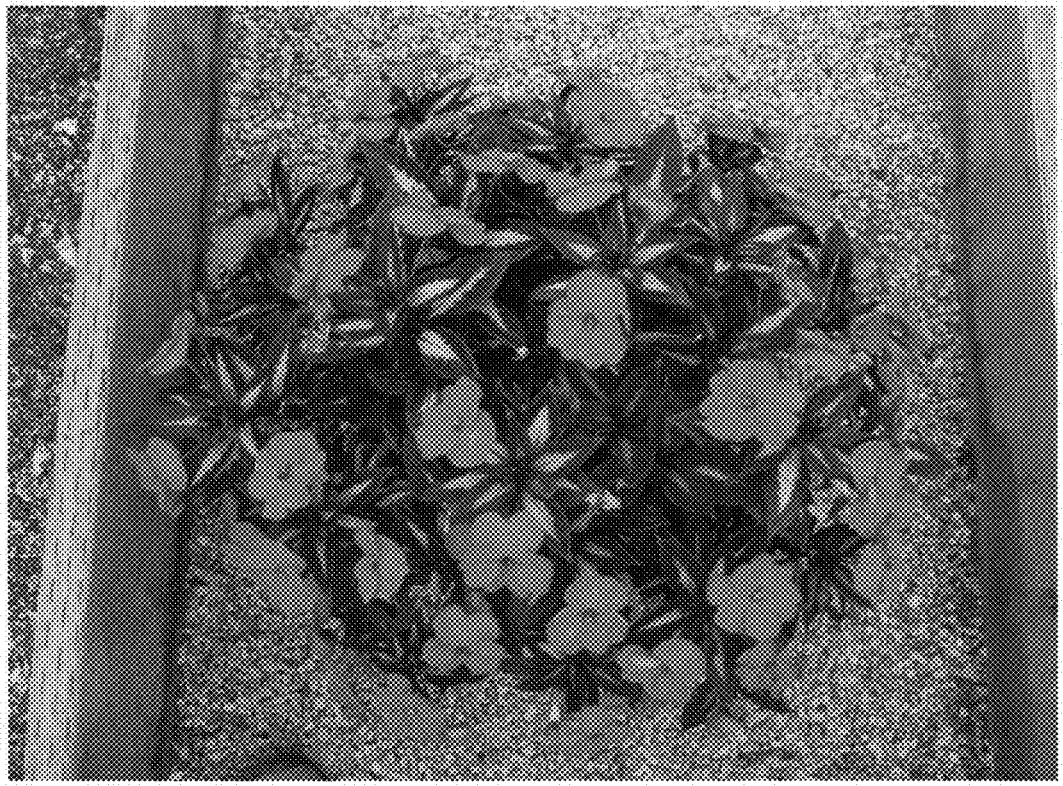
FIG. 1 shows the overall plant habit of the plant grown in a pot.
Figure 2:
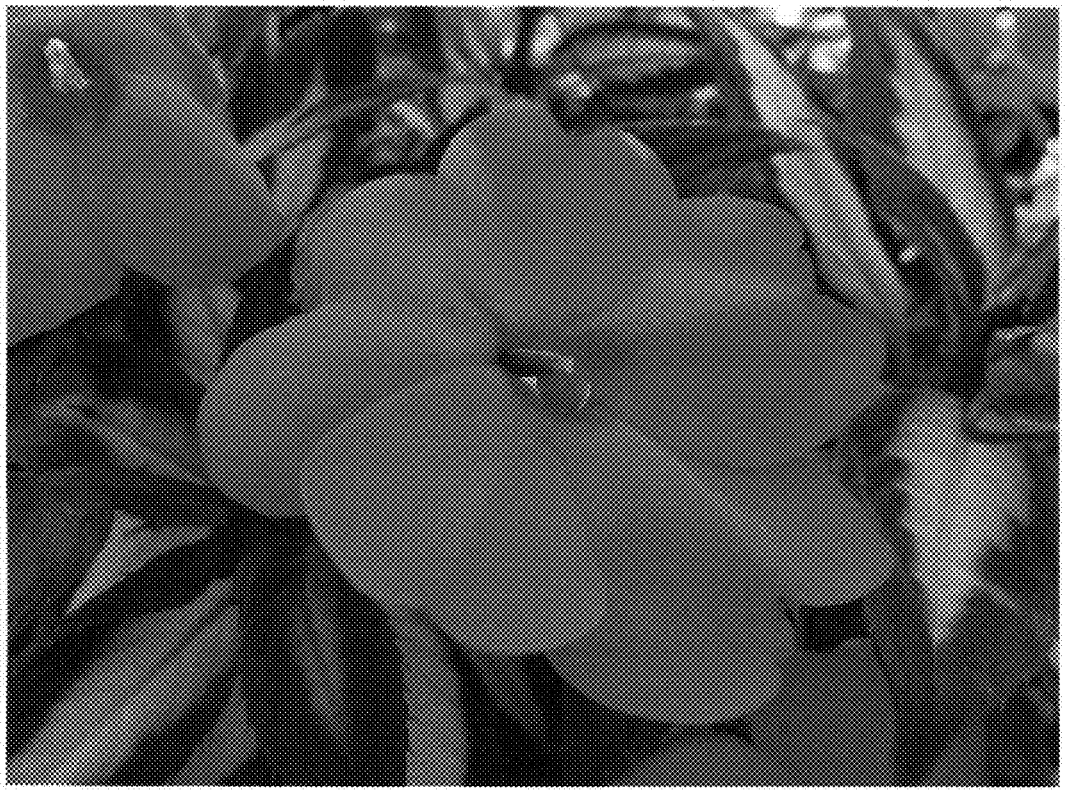
FIG. 2 shows a close-up of the mature inflorescence of the plant.

The following detailed descriptions set forth the distinctive characteristics of 'SAKIMP038'. Data was obtained from plants grown about 2 months from propagation by terminal cuttings in Salinas, Calif. under greenhouse conditions. Color references are to The Royal Horticultural Society of London Colour Chart (R.H.S.), 4$^{th}$ edition (2001). Anatomic labels are from *The Cambridge Illustrated Glossary of Botanical Terms*, by M. Hickey and C. King, Cambridge University Press.

Classification:

*Family*.—Balsaminaceae.
*Botanical*.—*Impatiens×hybrida* hort.
*Common*.—*Impatiens*.
*Designation*.—'SAKIMP038'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Parentage:

*Female parent*.—The proprietary *Impatiens* plant line 'NG-02SM-13'.

*Male parent*.—The proprietary *Impatiens* plant line 'NF-457BB'.

Plant description:

*Habit*.—Spreading.

*Height*.—21.5 cm from the soil line to the top of the foliage.

*Spread*.—42.0 cm.

*Number of branches*.—10 total with 1 main branch.

*Length of branches*.—1.5 cm from the soil line to the first node, 17.0 cm total.

*Diameter of branches*.—1.3 cm for the main branch, 6.0 mm to 8.0 mm for the other secondary branches.

*Color of branches*.—Closest to but darker than RHS 187A (Greyed-Purple).

*Life cycle*.—Annual.

*Time to produce a rooted cutting*.—About 4 weeks.

*Time to bloom from propagation*.—6 to 8 weeks.

*Flowering requirements (season)*.—Will flower so long as temperature is above 5° C.

*Temperature tolerances*.—Plants observed to continue flowering in a temperature range of 5° C. to 36° C.

Stems:

*Color*.—Closest to RHS 187B (Greyed-Purple).

*Anthocyanin color*.—RHS 187B (Greyed-Purple).

*Pubescence*.—Absent.

*Description*.—Strong; circular cross-section, smooth and shiny.

*Length*.—4.0 cm to 8.0 cm from the first to the second node, 12.0 cm to 15.0 cm total.

*Diameter*.—5.0 mm to 7.0 mm.

*Internode length*.—3.5 cm to 4.0 cm.

Leaves:

*Arrangement*.—Whorled with up to 5 leaves per node, opposite if only two leaves at one node.

*Shape*.—Lanceolate, curled.

*Apex*.—Acuminate.

*Base*.—Shortly attenuate.

*Margin*.—Serrate.

*Surface appearance*.—Dull; waxy.

*Length*.—8.3 cm.

*Width*.—3.7 cm.

*Color*.—Upper surface: RHS 139A (Green) with RHS 4A (Yellow) at the mid-vein; on mature leaves this color is slightly lighter RHS 11B (Yellow). Lower surface: RHS 147B (Yellow-Green) with RHS 11C (Yellow) at mid-vein.

*Variegation*.—Present.

*Fragrance*.—Absent.

*Surface pubescence*.—Absent.

*Petiole*.—Length: 1.0 cm. Diameter: 3.0 mm. Color: RHS 187C (Greyed-Purple). Texture: Smooth, glabrous.

*Venation pattern*.—Pinnate.

*Venation color*.—Upper surface: Closest to RHS 62D (Red-Purple). Lower surface: RHS 60A (Red-Purple).

Flowers:

*Number of flowers per node*.—1 to 3 in bloom at one time; about 10 flower buds.

*Number of flowers per plant*.—Approximately 35 in bloom.

*Lastingness of individual blooms on the plant*.—14 days.

*Inflorescence type*.—Single flower with spur.

*Fragrance*.—Absent.

Corolla:

*Corolla shape*.—Roughly circular with 5 radial petals.

*Corolla diameter*.—5.8 cm.

*Corolla depth*.—1.0 cm.

*Petals*.—Surface texture (both surfaces): Glabrous. Length: 3.0 cm. Width: 3.1 cm. Shape: Obcordate. Apex: Emarginate (cleaved). Margin: Entire. Base: Attenuate. Color: Upper surface: RHS N30A (Orange-Red). Lower: Closest to RHS 39A (Red). Eye zone: Closest to RHS 60A (Red-Purple).

Calyx:

*Sepal shape*.—Lanceolate.

*Sepal number*.—2.

*Sepal color*.—Upper surface: Closest to 180A (Greyed-Red) with very slight RHS 147A at the tip. Lower surface: Closest to RHS 157A (Green-White) with very slight RHS 180A (Greyed-Red).

*Sepal length*.—1.5 cm.

*Sepal diameter*.—6.0 mm.

*Sepal base*.—Subcordate.

*Sepal apex*.—Caudate.

*Sepal margin*.—Entire.

*Sepal texture*.—Glabrous.

Bud:

*Surface texture*.—Glabrous.

*Length*.—2.2 cm.

*Diameter*.—1.4 cm.

*Shape*.—Deltoid longitudinal cross-section.

*Color*.—Closest to RHS 41A (Red) with RHS 183A (Greyed-Purple) at the edge and very slight 144A (Yellow-Green) at the edge.

Peduncle:

*Length*.—3.0 cm.

*Color*.—Closest to RHS 185A (Greyed-Purple).

*Diameter*.—2.0 mm.

*Surface texture*.—Smooth, glabrous.

Spur:

*Color*.—Closest to RHS 60A (Red-Purple) with N77A (Purple) at the tip and N155B (White) at the base with RHS 60B (Red-Purple) at the midpoint of the base and RHS 143B (Yellow-Green) at the tip of base.

*Shape*.—Tubular; curved downward.

*Length*.—6.5 cm.

*Diameter*.—1.0 mm to 2.0 mm.

Reproductive organs:

*Stamens*.—Stamen form: Fused; split into 4 lobes. Stamen number: 5. Filament form: Free. Filament length: 7.0 mm. Filament color: RHS 144C (Yellow-Green). Anther length: 7.0 mm. Anther color: Closest to RHS 50A (Red). Pollen amount: Abundant. Pollen color: 158B (Yellow-White). Pollen description: Powdery.

*Pistil*.—Pistil number: 1. Stigma color: Closest to 145D (Yellow-Green). Style color: RHS 136A (Green). Ovary arrangement: Parietal. Ovary interior color: RHS 145B (Yellow-Green).

*Seed production*.—Not present.

Disease and insect resistance: No particular resistance or susceptibility observed.

COMPARISON WITH PARENTAL LINES AND COMMERCIAL VARIETY

'SAKIMP038' is distinguished from its parents as shown in Table 1 below:

TABLE 1

Comparison with Parental Lines

| Characteristic | 'SAKIMP038' | Female Parent 'NG-02SM-13' | Male Parent 'NF-457BB' |
|---|---|---|---|
| Flower color | Orange-red with red-purple eyes | Deeper orange than 'SAKIMP038' | Magenta |
| Leave variegation | Present | Absent | Absent |

When 'SAKIMP038' is compared to the commercial *Impatiens* variety 'SAKIMP026' (U.S. Plant Pat. No. 24,321), the following differences are as described in Table 2 below.

TABLE 2

Comparison with Similar Variety

| Characteristic | 'SAKIMP038' | 'SAKIMP026' |
|---|---|---|
| Growth habit | Spreading | Compact |
| Petal color, upper surface | RHS N30A (Orange-Red) | RHS 40A (Red) |
| Spur color | Closest to RHS 60A (Red-Purple) with N77A (Purple) at the tip and N155B (White) at the base with RHS 60B (Red-Purple) at the midpoint of base and RHS 143B (Yellow-Green) at tip of base | RHS 53D (Red) |
| Mature leaf color, upper surface | Variegated with RHS 139A (Green) with RHS 4A (Yellow) at the mid vein; on mature leaves this color is slightly lighter RHS 11B (Yellow) | Darker than RHS 147A (Yellow-Green) |

We claim:

1. A new and distinct variety of New Guinea *Impatiens* plant named 'SAKIMP038' as described and illustrated herein.

* * * * *